(12) United States Patent
Pochapin

(10) Patent No.: US 11,147,824 B1
(45) Date of Patent: Oct. 19, 2021

(54) COLONIC IRRIGATION COMPOSITION

(71) Applicant: New York University, New York, NY (US)

(72) Inventor: Mark Pochapin, New York, NY (US)

(73) Assignee: New York University, New York, NY (US)

( * ) Notice: Subject to any disclaimer, the term of this patent is extended or adjusted under 35 U.S.C. 154(b) by 682 days.

(21) Appl. No.: 15/730,480

(22) Filed: Oct. 11, 2017

Related U.S. Application Data

(60) Provisional application No. 62/406,651, filed on Oct. 11, 2016.

(51) Int. Cl.
| | |
|---|---|
| *A61K 31/695* | (2006.01) |
| *A61K 36/534* | (2006.01) |
| *A61K 9/08* | (2006.01) |
| *A61B 1/31* | (2006.01) |
| *C08L 83/04* | (2006.01) |
| *C09B 7/02* | (2006.01) |
| *C09B 21/00* | (2006.01) |
| *A61B 1/015* | (2006.01) |

(52) U.S. Cl.
CPC ............ *A61K 31/695* (2013.01); *A61B 1/015* (2013.01); *A61B 1/31* (2013.01); *A61K 9/08* (2013.01); *A61K 36/534* (2013.01); *C08L 83/04* (2013.01); *C09B 7/02* (2013.01); *C09B 21/00* (2013.01); *A61B 2217/007* (2013.01)

(58) Field of Classification Search
None
See application file for complete search history.

(56) References Cited

U.S. PATENT DOCUMENTS

| | | | |
|---|---|---|---|
| 2009/0297441 A1 * | 12/2009 | Canham | A61K 49/0043 424/1.61 |
| 2015/0224127 A1 | 8/2015 | Nizam | |
| 2015/0238635 A1 | 8/2015 | Kachaamy | |
| 2015/0320793 A1 | 11/2015 | Albrecht | |

* cited by examiner

*Primary Examiner* — Terry A McKelvey
*Assistant Examiner* — Catheryne Chen
(74) *Attorney, Agent, or Firm* — Hodgson Russ LLP

(57) ABSTRACT

Provided herein are clear aqueous colonoscopy irrigation compositions, and methods for visualization of colonic mucosa during colonoscopy procedure. The composition comprises indigo, blue or green colored contrast dye, polydimethylsiloxane, and muscle relaxant.

17 Claims, 1 Drawing Sheet

COLONIC IRRIGATION COMPOSITION

CROSS REFERENCE TO RELATED APPLICATIONS

This application claims priority to U.S. Provisional application No. 62/406,651, filed on Oct. 11, 2016, the disclosure of which is incorporated herein by reference.

BACKGROUND OF THE DISCLOSURE

Currently, colonoscopy is considered to be the most comprehensive method of colorectal cancer screening—allowing for the detection of potentially pre-cancerous adenomatous polyps. Colonoscopy has been shown to both prevent colorectal cancer and detect cancer early, as evidenced by dramatically declining incidence and mortality rates in recent years. As effective as colonoscopy is, a small percentage of polyps are missed. Further, colonic spasm often occurs as a consequence of colonic manipulation with the colonoscope.

Several compositions are known for preparing the gastrointestinal tract (GI tract) for colonoscopy. These compositions are taken orally by individuals over a period of 24 hours prior to the procedure and help to cleanse the GI tract of all food digestion materials including stools, gas and the like. During the colonoscopy procedure, however, a saline solution is typically used for irrigation.

SUMMARY OF THE DISCLOSURE

This disclosure provides a composition for use as an irrigation solution during colonoscopy procedure. The composition is termed herein as colonoscopy irrigation composition or colonoscopy irrigation solution. The composition is an aqueous composition and can comprise one or more of a surfactant, a muscle relaxant, and a dye. For example, the surfactant can be simethicone, the muscle relaxant can be peppermint oil, and the dye can be an indigo, blue or green colored contrast dye. The colonoscopy irrigation composition can be used during the colonoscopy procedure to aid in the live examination of the colonic mucosal surface.

DETAILED DESCRIPTION OF THE DISCLOSURE

Figure 1A:
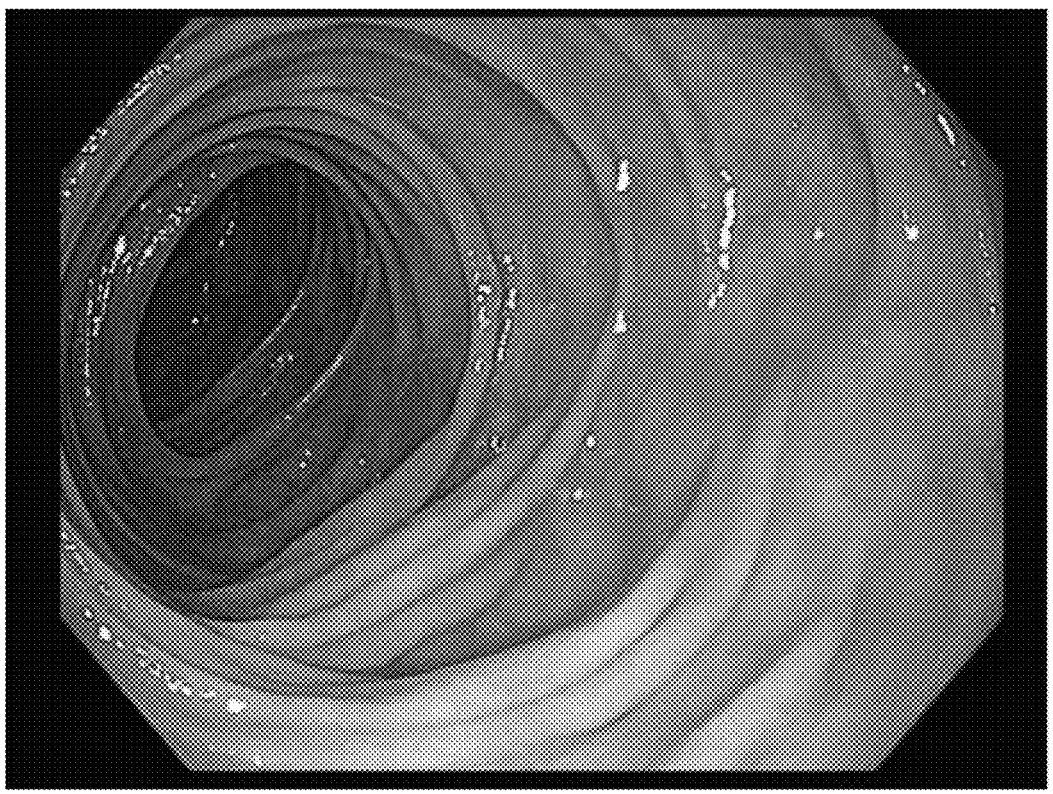
FIG. 1A is an image obtained during colonoscopy.

The present disclosure provides an aqueous composition comprising, consisting essentially of, or consisting of one or more of: a dye, a surfactant, and a muscle relaxant. For example, the composition can comprise or consist essentially of: one or more indigo, blue or green dyes, one or more surfactants, and one or more muscle relaxants. In one embodiment, the composition can comprise or consist essentially of: one or more indigo, blue or green dyes, and one or more surfactants. One or more of the components can be aromatic. The components can be present in a solvent, which may be a pharmaceutical carrier. The description below provides several examples of the components in 1 liter of a solvent (meaning the component amounts are provided per liter of the solvent).

In one embodiment, the present composition comprises a dye and a surfactant, which may be present in a pharmaceutical carrier. In one embodiment, the present composition comprises a dye and a muscle relaxant.

The compositions can be used as an irrigation liquid during colonoscopy procedure. For example, the compositions are useful for trans-rectal preps or irrigation during colonoscopy. It is considered that these compositions would not be useful for oral preps of individuals prior to colonoscopy.

Suitable surfactants include polydimethylsiloxanes. For example, dimethicone or simethicone can be used. Simethicone is a mixture of polydimethylsiloxane and silicon dioxide. It acts as a surfactant in the composition. It helps to prevent gas pockets in the intestinal tract. Although simethicone has been used in colonoscopy prep compositions, it has not been used for colonoscopy irrigation compositions. During the colonoscopy procedure, in the present disclosure, it is considered the surfactant helps to eliminate or minimize bubbles so that the mucosal surface of the colon can be visualized effectively.

Simethicone is available under several brand names including Equalizer® Gas Relief (OTC); Gas-X® (OTC); Infantaire™ Gas Drops (OTC); Mylanta®; Mylicon® Infants (OTC); Phazyme®.

The amount of the surfactant, such as simethicone, in the composition can be from 25 to 35 mg per liter. For example, the concentration can be 25, 26, 27, 28, 29, 30, 31, 32, 33, 34 or 35 mg/liter. It can be from 20 to 40 mg/liter (and all integer values therebetween). However, it is preferred not to have concentrations of surfactant, such as simethicone, higher than 40 mg/liter as it may make the composition cloudy. For example, in one embodiment, the concentration of the surfactant, such as simethicone, is not higher than 35 mg/liter. While this is not a concern for use in colonoscopy prep compositions—and in fact, it is used at higher concentrations in the colonoscopy prep solutions —, it renders the colonoscopy irrigation composition turbid and turbidity obscures visualization of the GI mucosal surface. It is therefore not desirable to use simethicone at concentrations at which it will render the composition turbid or cloudy.

The composition comprises a dye which is in the indigo, blue, or green range of the spectrum. Examples of suitable dyes include indigo carmine and methylene blue. The amount of the dye can be from 0.2 to 1.5 ml (of a 1% solution) per liter (providing a final concentration of 0.0002% to 0.0015%) and all ranges and values therebetween to the tenth or the hundredth decimal place. For example, the amount of the dye can be 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, or 1.5 ml/liter using a 1% solution. In one embodiment, the amount of dye can be more than 1.5 ml/liter of a 1% solution. For example, the amount of dye can be from 0.2 ml/liter to 5.0 ml/liter (of a 1% solution). Further examples of the amount of dye are 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0/ml per liter of a 1% solution. These dyes are commercially available. The amount of dye used in the present composition is lower than that used as a spray to stain the mucosal surface cells. For example, typically, a 1.0% methylene blue is used for spraying currently. Hence it was surprising that a lower concentration was found to be useful for staining of polyps during the procedure. For example, the concentrations used in the present disclosure can be about or more than a 100 times lower than used currently. For example, the concentrations of the dye can be about or more than a 1000 times lower than used currently.

The composition can comprise a muscle relaxant. An example of a natural muscle relaxant is peppermint oil, which also provides a desirable aroma. The desirable aroma may be pleasing to the patient upon awakening.

The amount of peppermint oil in the composition can be from 0.25 to 0.75 (and all values to the tenth or the hundredth decimal place therebetween) ml/liter. The amount of peppermint oil (i.e., the muscle relaxant) can be more than 0.75 m/liter. For example, the peppermint oil in the composition can be up to 5.0 ml/liter. Peppermint oil can be from 0.25 to 5.0 (and all values to the tenth or the hundredth decimal place therebetween) ml/liter Examples include 0.25, 0.5, 0.75, 1.0, 1.5, 2.0, 2.5, 3.0, 3.5, 4.0, 4.5, and 5.0 ml/liter.

The composition can comprise a solvent as a pharmaceutical carrier, such as, for example, water or normal saline (0.9% sodium chloride). The compositions of the present disclosure are clear (no turbidity), aqueous compositions.

In one embodiment, the present composition comprises or consists essentially of from 25-35 mg surfactant, from 0.25 to 5.0 ml of a 1% solution of dye, and from 0.25 to 5.0 ml of muscle relaxant per liter of a pharmaceutical carrier. For example, the present composition can comprise from 25-35 mg polydimethylsiloxane, from 0.25 to 5.0 ml of a 1% solution of methylene blue or indigo carmine dye, and from 0.25 to 5.0 ml of peppermint per liter of a pharmaceutical carrier.

In one embodiment, the present composition comprises or consists essentially of from 25-35 mg surfactant, from 0.25 to 2.5 ml of a 1% solution of dye, and from 0.25 to 2.5 ml of peppermint oil in one liter of a pharmaceutical carrier.

In one embodiment, the present composition comprises or consists essentially of from 25-35 mg surfactant, from 0.25 to 1.5 ml of a 1% solution of dye, and from 0.25 to 0.75 ml of peppermint oil in one liter of a pharmaceutical carrier.

In one embodiment, the composition comprises or consists essentially of from 25-35 mg polydimethylsiloxane, from 0.25 to 1.5 ml of a 1% solution of methylene blue or indigo carmine dye, and from 0.25 to 0.75 ml of peppermint oil in one liter of normal saline or water.

In one embodiment, the composition comprises or consists essentially of from 25-35 mg simethicone, from 0.25 to 1.5 ml of a 1% solution of methylene blue or indigo carmine dye, and from 0.25 to 0.75 ml of peppermint oil in one liter of normal saline or water.

In one embodiment, the composition comprises or consists essentially of from 28-33 mg simethicone, from 0.3 to 0.8, or 0.4 to 0.6 ml of a 1% solution of methylene blue or indigo carmine dye, and from 0.4 to 0.6 ml of peppermint oil in one liter of normal saline or water.

In one embodiment, the composition comprises or consists essentially of 30 mg simethicone, 0.5 ml of a 1% solution of methylene blue or indigo carmine dye, and 0.5 ml of peppermint oil in one liter of normal saline or water.

In one embodiment, the composition comprises or consists essentially of from 25-35 mg simethicone and from 0.25 to 0.75 ml of peppermint oil, and optionally, from 0.25 to 1.5 ml of a 1% solution of methylene blue or indigo carmine dye in one liter of normal saline or water.

In one embodiment, the composition comprises or consists essentially of from 28-33 mg simethicone and from 0.4 to 0.6 ml of peppermint oil, and optionally, from 0.3 to 0.8 or 0.4 to 0.6 ml of a 1% solution of methylene blue or indigo carmine dye in one liter of normal saline or water.

In one embodiment, the composition comprises or consists essentially of 30 mg simethicone and 0.5 ml of peppermint oil, and optionally, 0.5 ml of a 1% solution of methylene blue or indigo carmine dye in one liter of normal saline or water.

In one embodiment, the composition comprises or consists essentially of from 25-35 mg simethicone and from 0.25 to 1.5 ml of a 1% solution of methylene blue or indigo carmine dye, and, optionally, from 0.25 to 0.75 ml of peppermint oil in one liter of normal saline or water.

In one embodiment, the composition comprises or consists essentially of from 28-33 mg simethicone and from 0.3 to 0.8 or 0.4 to 0.6 ml of 1% solution of methylene blue or indigo carmine dye, and optionally, from 0.4 to 0.6 ml of peppermint oil in one liter of normal saline or water.

In one embodiment, the composition comprises or consists essentially of 30 mg simethicone and 0.5 ml of a 1% solution of methylene blue or indigo carmine dye, and optionally, 0.5 ml of peppermint oil in one liter of normal saline or water.

In one embodiment, the present composition comprises or consists essentially of from 25-35 mg surfactant and from 0.25 to 1.5 ml of a 1% solution of dye in one liter of a pharmaceutical carrier.

In one embodiment, the composition comprises or consists essentially of from 25-35 mg polydimethylsiloxane and from 0.25 to 1.5 ml of a 1% solution of methylene blue or indigo carmine dye in one liter of normal saline or water.

In one embodiment, the composition comprises or consists essentially of from 25-35 mg simethicone and from 0.25 to 1.5 ml of a 1% solution of methylene blue or indigo carmine dye in one liter of normal saline or water.

In one embodiment, the composition comprises or consists essentially of from 28-33 mg simethicone and from 0.3 to 0.8 or 0.4 to 0.6 ml of a 1% solution of methylene blue or indigo carmine dye in one liter of normal saline or water.

In one embodiment, the composition comprises or consists essentially of 30 mg simethicone and 0.5 ml of a 1% solution of methylene blue or indigo carmine dye in one liter of normal saline or water.

The composition can be provided in a liquid form or a powdered (solid) form. If in a powdered form, the surfactant, dye and peppermint oil can be provided separately (independently or combined) from the solvent. The composition may be provided in a tablet, or capsule form or a soft-gel form. At the time of use, the surfactant, dye and peppermint oil can be added to the solvent. In one embodiment, all the components can be provided separately and can be combined at the time of use. The components, either alone or combined, can be provided in a kit form. Thus, the present disclosure also provides kits for use as colonoscopy irrigation compositions. The kit can comprise the surfactant, dye, and peppermint oil, either separately or combined, and the appropriate amount of solvent. For example, the components may be in a tablet, capsule, or soft-gel and the kit can include a sterile saline solution, which can be combined just before use. A kit may contain sufficient amounts of the components for one procedure, or for several procedures. The kit can also contain instructions on mixing of the components and instructions for use.

The amount of the irrigation composition needed during a colonoscopy procedure can vary. For example, it can be from about 500 mls to about 2 liters or any amount therebetween. Higher or lower volumes may be used as deemed appropriate by the clinician. For example, a volume of about 200 mls to about 3 liters (or any amount therebetween) may be used.

The present colonoscopy irrigation composition allows for enhanced visualization of difficult-to-see polyps (including flat and depressed lesions). Increased detection and removal of pre-cancerous polyps will result in further reductions in colorectal cancer incidence and mortality rates. At the same time, any bubble formation is reduced and the colon and rectum are relaxed during the colonoscopy.

For carrying out the colonoscopy procedure, the colon (or other GI tract) is cleared of stool, bile, mucus and other secretions by oral consumption of colonoscopy prep compositions. This renders the colon substantially or completely free of stool and other materials and makes it amenable for colonoscopy. During the procedure, the present composition can be delivered through a working channel in a colonoscope. For example, a water pump can be used where a pump is operably connected to a container and a conduit within the colonoscope. The container can contain the present colonic irrigation composition. The pump enables delivery of the composition to the areas in immediate vicinity of the tip of the colonoscope. As the colonoscope is guided to desired areas, the composition can be delivered as desired. The solution can be delivered through the working channel of the scope or a dedicated water jet from the tip of the scope.

During the colonoscopy procedure, a desired or selected amount of the irrigation composition can be ejected continuously or intermittently at a location in the GI tract. For example, about 20 to 100 mls of the composition may be ejected continuously or intermittently. In one embodiment, about 50-70 mls of the composition may be ejected. As the scope is moved within the colon to other locations, more of the composition may be ejected as desired. The total volume of the composition used during colonoscopy is not limiting and it may be varied as deemed appropriate by a clinician. A typical total volume may be from about 200 mls to about 3 liters. Other total volume ranges include from about 500 mls to about 2.5 liters, from about 250 mls to about 2.0 liter, from about 250 mls to about 3 liters, from about 500 mls to about 1.5 liter, and from about 500 mls to about 1.0 liter. Lower or higher volumes may be used. In one embodiment, the total volume may be about 500 mls, about 1.0 liter, about 1.5 liter, about 2.0 liter, about 2.5 liter, or about 3.0 liter, or more.

The examination of the colonic mucosal surface can be carried out live as the irrigation solution is being pumped into the area, or the images can be captured on a storage medium and the images can be viewed later.

The disclosure is further described by the following example, which is intended to be illustrative and not limiting in any way.

Example 1

Figure 1B:
FIG. 1B is the image of the same colon (as in FIG. 1A) using the irrigation composition of the present disclosure. A polyp can be seen in the lower right hand corner—indicated by a circle drawn around it.

In an example, a composition comprising the dye methylene blue and simethicone was used for irrigation in a colonoscopy procedure. The composition comprised 30 mg simethicone and 0.5 ml of a 1% solution of methylene blue in one liter of normal saline or water. In one example, the composition was made up of 30 mg simethicone and 0.5 ml of a 1% solution of methylene blue, and 0.5 ml peppermint oil. Use of this composition provided clear visualization of the mucosal surface of the colon and enhanced visualization of anything that deforms the surface topography of the colonic mucosa, such as, for example, a polyp (FIG. 1B). For comparison, an image of the same colon is without the present irrigation solution is shown in FIG. 1A.

What is claimed is:

1. An aqueous, clear composition for irrigation during a colonoscopy procedure comprising:
   a) indigo, blue, or green colored contrast dye;
   b) a surfactant comprising polydimethylsiloxane; and
   c) muscle relaxant,
   present in a solvent.

2. The composition of claim 1, wherein the surfactant is simethicone.

3. The composition of claim 1, wherein the muscle relaxant is peppermint oil.

4. The composition of claim 1, wherein the dye is indigo carmine or methylene blue.

5. The composition of claim 2 wherein the dye is indigo carmine or methylene blue and the concentration of the dye is from 0.25 to 5.0 ml of a 1% solution/liter; the concentration of the simethicone is from 25 to 35 mg/liter; and the muscle relaxant is peppermint oil and the concentration of the peppermint oil is 0.25 to 5.0 ml/liter, and wherein the solvent is water or saline.

6. The composition of claim 2 wherein the dye is indigo carmine or methylene blue and the concentration of the dye is from 0.25 to 2.5 ml of a 1% solution/liter; the concentration of the simethicone is from 25 to 35 mg/liter; and the muscle relaxant is peppermint oil and the concentration of the peppermint oil is 0.25 to 2.5 ml/liter, and wherein the solvent is water or saline.

7. The composition of claim 2 wherein the dye is indigo carmine or methylene blue and the concentration of the dye is from 0.25 to 1.5 ml of a 1% solution/liter; the concentration of the simethicone is from 25 to 35 mg/liter; and the muscle relaxant is peppermint oil and the concentration of the peppermint oil is 0.25 to 0.75 ml/liter, and wherein the solvent is water or saline.

8. The composition of claim 5, wherein the composition comprises per liter of water or saline:
   a) 0.4 to 0.6 ml of methylene blue of a 1% solution;
   b) 28 to 33 mg of simethicone; and
   c) 0.4 to 0.6 ml peppermint oil.

9. The composition of claim 8, wherein the composition comprises per liter of water or saline:
   a) 0.5 ml of methylene blue of a 1% solution;
   b) 30 mg of simethicone; and
   c) 0.5 ml peppermint oil.

10. A method for examination of a colonic surface during a colonoscopy procedure comprising:
    a) administering to an individual undergoing the colonoscopy procedure a composition of claim 1 through a delivery channel in a colonoscope to a location in the colon of the individual such that the composition comes in contact with the colonic surface; and
    b) examining the colonic surface using the colonoscope.

11. The method of claim 10, wherein a volume of from 20 to 100 mls of the composition is ejected at the location in the colon.

12. The method of claim 11, wherein the composition is administered continuously or intermittently.

13. The method of claim 10, wherein the composition is delivered to multiple locations in the colon.

14. A kit comprising:
    a) a container containing simethicone;
    b) a container containing a dye selected from the group consisting of indigo carmine and methylene blue;
    c) a container containing peppermint oil;

d) a container containing sterile water or saline in sufficient amount for mixing the simethicone, dye, and peppermint oil sufficient to prepare a colonoscopy irrigation solution in which the simethicone is from 25 to 35 mg/liter, the dye is from 0.25 to 5.0 ml of a 1% solution/liter, and the peppermint oil is from 0.25 to 5.0 ml/liter; and e) optionally, instructions for making and using the colonoscopy irrigation solution.

15. The kit of claim 14, wherein simethicone, dye, and peppermint oil are in sufficient amounts to prepare a colonoscopy irrigation solution in which the simethicone is from 25 to 35 mg/liter, the dye is from 0.25 to 2.5 ml of a 1% solution/liter, and the peppermint oil is from 0.25 to 2.5 ml/liter of water or saline.

16. The kit of claim 15, wherein simethicone, dye, and peppermint oil are in sufficient amounts to prepare a colonoscopy irrigation solution in which the simethicone is from 25 to 35 mg/liter, the dye is from 0.25 to 1.5 ml of a 1% solution/liter, and the peppermint oil is from 0.25 to 0.75 ml/liter.

17. The kit of claim 14, wherein the simethicone, the dye and the peppermint oil are provided in the same container.

\* \* \* \* \*